United States Patent
Zhu

(10) Patent No.: US 12,043,657 B2
(45) Date of Patent: Jul. 23, 2024

(54) HUMAN COLLAGEN 17-TYPE POLYPEPTIDE, PRODUCTION METHOD THEREFOR AND USE THEREOF

(71) Applicant: SHANXI JINBO BIO-PHARMACEUTICAL CO., LTD., Shanxi (CN)

(72) Inventor: Yun Zhu, Beijing (CN)

(73) Assignee: SHANXI JINBO BIO-PHARMACEUTICAL CO., LTD., Shanxi (CN)

( * ) Notice: Subject to any disclaimer, the term of this patent is extended or adjusted under 35 U.S.C. 154(b) by 84 days.

(21) Appl. No.: 17/761,992

(22) PCT Filed: Oct. 26, 2020

(86) PCT No.: PCT/CN2020/123600
§ 371 (c)(1),
(2) Date: Mar. 18, 2022

(87) PCT Pub. No.: WO2021/083072
PCT Pub. Date: May 6, 2021

(65) Prior Publication Data
US 2022/0348639 A1    Nov. 3, 2022

(30) Foreign Application Priority Data
Oct. 31, 2019   (CN) .......................... 201911051106.3

(51) Int. Cl.
C07K 14/78     (2006.01)
A61K 8/65      (2006.01)
A61Q 19/00     (2006.01)
A61K 38/00     (2006.01)

(52) U.S. Cl.
CPC ................ C07K 14/78 (2013.01); A61K 8/65 (2013.01); A61Q 19/00 (2013.01); A61K 38/00 (2013.01)

(58) Field of Classification Search
CPC .................................. C07K 14/78; A61K 8/65
See application file for complete search history.

(56) References Cited

U.S. PATENT DOCUMENTS

2007/0083334 A1* 4/2007 Mintz ................ G16B 40/00
                                                     702/19
2013/0237486 A1* 9/2013 Bella ..................... C07K 14/78
                                                    435/254.2

FOREIGN PATENT DOCUMENTS

CN      110845603 A       2/2020
WO      WO 2012/063088 A1   5/2012
WO      WO 2012063088 A2    5/2012
WO      WO 2019057704 A1    3/2019

OTHER PUBLICATIONS

Areida et al., 2001, Properties of the Collagen Type XVII Ectodomain, The Journal of Biological Chemistry, 12: 1594-1601.*
PCT/CN2020/123600, International Search Report and Written Opinion dated Jan. 21, 2021; 7 pages.
Li, K. et al. "Genomic organization of collagenous domains and chromosomal assignment of human 180-kDa bullous pemphigoid antigen-2, a novel collagen of stratified squamous epithelium", The Journal of Biological Chemistry, vol. 266, No. 35, Dec. 15, 1991 (Dec. 15, 1991), pp. 24064-24069.
Japanese Patent Application No. JP2022-518672, Office Action dated Mar. 22, 2023, with English translation 11 pages.
Japanese Patent Application No. JP2022-518672, Decision to Grant a Patent dated Jun. 7, 2023, with English translation, 5 pages.
Japanese Patent Application No. JP2022-518672 English translation of Allowed Claims as of Jun. 7, 2023, 3 pages.
Yao, J. et al., Design, expression and characterization of collagen-like proteins based on the cell adhesive and crosslinking sequences derived from native collagens, J. Biochem., Nov. 2004, 136(5): pp. 643-649.

* cited by examiner

*Primary Examiner* — Amber D Steele
(74) *Attorney, Agent, or Firm* — COZEN O'CONNOR

(57) ABSTRACT

Provided is a polypeptide, a production method therefor and a use thereof. The polypeptide includes 63 to 1496 continuous amino acid residues of SEQ ID NO: 9, and includes a sequence represented by $(A)_m$ or is composed of the sequence represented by $(A)_m$, wherein each A is an amino acid sequence selected from any one of those represented by SEQ ID NO: 1, SEQ ID NO: 2 and SEQ ID NO: 3, or a modified amino acid sequence or a sequence variant thereof; m is an integer between 1 and 10; and each A is the same or different and two adjacent As are directly connected by peptide bonds or connected by at least one amino acid residue, wherein the polypeptide has a cell adhesion activity, and a method of producing said polypeptide and use of said polypeptide.

8 Claims, 2 Drawing Sheets
Specification includes a Sequence Listing.

SEQUENCE LISTING

<160> NUMBER OF SEQ ID NOS: 9

<210> SEQ ID NO 1
<211> LENGTH: 69
<212> TYPE: PRT
<213> ORGANISM: Artificial Sequence
<220> FEATURE:
<223> OTHER INFORMATION: C17A

<400> SEQUENCE: 1

Gly Ser Pro Gly Pro Lys Gly Asp Met Gly Ser Pro Gly Pro Lys Gly
1               5                   10                  15

Asp Arg Gly Phe Pro Gly Thr Pro Gly Ile Pro Gly Pro Leu Gly His
            20                  25                  30

Pro Gly Pro Gln Gly Pro Lys Gly Gln Lys Gly Ser Val Gly Asp Pro
        35                  40                  45

```
Gly Met Glu Gly Pro Met Gly Gln Arg Gly Arg Gly Pro Met Gly
            50                  55                  60

Pro Arg Gly Glu Ala
 65
```

<210> SEQ ID NO 2
<211> LENGTH: 63
<212> TYPE: PRT
<213> ORGANISM: Artificial Sequence
<220> FEATURE:
<223> OTHER INFORMATION: C17B

<400> SEQUENCE: 2

```
Gly Leu Gln Gly Leu Arg Gly Glu Val Gly Leu Pro Gly Val Lys Gly
 1               5                  10                  15

Asp Lys Gly Pro Met Gly Pro Pro Gly Pro Lys Gly Asp Gln Gly Glu
                20                  25                  30

Lys Gly Pro Arg Gly Leu Thr Gly Glu Pro Gly Met Arg Gly Leu Pro
            35                  40                  45

Gly Ala Val Gly Glu Pro Gly Ala Lys Gly Ala Met Gly Pro Ala
        50                  55                  60
```

<210> SEQ ID NO 3
<211> LENGTH: 119
<212> TYPE: PRT
<213> ORGANISM: Artificial Sequence
<220> FEATURE:
<223> OTHER INFORMATION: C17C1

<400> SEQUENCE: 3

```
Gly Ala Asp Phe Ala Gly Asp Leu Asp Tyr Asn Glu Leu Ala Val Arg
 1               5                  10                  15

Val Ser Glu Ser Met Gln Arg Gln Gly Leu Leu Gln Gly Met Ala Tyr
                20                  25                  30

Thr Val Gln Gly Pro Pro Gly Gln Pro Gly Pro Gln Gly Pro Pro Gly
            35                  40                  45

Ile Ser Lys Val Phe Ser Ala Tyr Ser Asn Val Thr Ala Asp Leu Met
 50                  55                  60

Asp Phe Phe Gln Thr Tyr Gly Ala Ile Gln Gly Pro Pro Gly Gln Lys
 65                  70                  75                  80

Gly Glu Met Gly Thr Pro Gly Pro Lys Gly Asp Arg Gly Pro Ala Gly
                85                  90                  95

Pro Pro Gly His Pro Gly Pro Gly Pro Arg Gly His Lys Gly Glu
                100                 105                 110

Lys Gly Asp Lys Gly Asp Gln
        115
```

<210> SEQ ID NO 4
<211> LENGTH: 207
<212> TYPE: PRT
<213> ORGANISM: Artificial Sequence
<220> FEATURE:
<223> OTHER INFORMATION: C17A3

<400> SEQUENCE: 4

```
Gly Ser Pro Gly Pro Lys Gly Asp Met Gly Ser Pro Gly Pro Lys Gly
 1               5                  10                  15

Asp Arg Gly Phe Pro Gly Thr Pro Gly Ile Pro Gly Pro Leu Gly His
                20                  25                  30
```

Pro Gly Pro Gln Gly Pro Lys Gly Gln Lys Gly Ser Val Gly Asp Pro
         35                  40                  45

Gly Met Glu Gly Pro Met Gly Gln Arg Gly Arg Glu Gly Pro Met Gly
     50                  55                  60

Pro Arg Gly Glu Ala Gly Ser Pro Gly Pro Lys Gly Asp Met Gly Ser
65                  70                  75                  80

Pro Gly Pro Lys Gly Asp Arg Gly Phe Pro Gly Thr Pro Gly Ile Pro
             85                   90                  95

Gly Pro Leu Gly His Pro Gly Pro Gln Gly Pro Lys Gly Gln Lys Gly
         100                 105                 110

Ser Val Gly Asp Pro Gly Met Glu Gly Pro Met Gly Gln Arg Gly Arg
     115                 120                 125

Glu Gly Pro Met Gly Pro Arg Gly Glu Ala Gly Ser Pro Gly Pro Lys
    130                 135                 140

Gly Asp Met Gly Ser Pro Gly Pro Lys Gly Asp Arg Gly Phe Pro Gly
145                 150                 155                 160

Thr Pro Gly Ile Pro Gly Pro Leu Gly His Pro Gly Pro Gln Gly Pro
             165                 170                 175

Lys Gly Gln Lys Gly Ser Val Gly Asp Pro Gly Met Glu Gly Pro Met
         180                 185                 190

Gly Gln Arg Gly Arg Glu Gly Pro Met Gly Pro Arg Gly Glu Ala
     195                 200                 205

<210> SEQ ID NO 5
<211> LENGTH: 621
<212> TYPE: DNA
<213> ORGANISM: Artificial Sequence
<220> FEATURE:
<223> OTHER INFORMATION: C17A3-DNA

<400> SEQUENCE: 5
ggtagcccag gtccaaaagg tgatatggga agcccaggtc cgaaaggtga tcgtggtttt    60
ccgggtacac caggtattcc gggtccactg gtcatccag gtccgcaagg tccgaaaggc   120
cagaaaggta gcgtgggtga tccgggtatg aagggccta tggggcagcg tgggcgtgaa   180
gggccgatgg gtccgcgtgg tgaagcaggt agcccggggc ctaaagggga tatggggagt   240
ccgggtccga agggggatcg tggatttccg ggtacgccgg gtatcccggg tccgctgggt   300
catccgggtc cgcaagggcc taaaggtcag aaaggtagtg tgggtgatcc tggtatggaa   360
ggtccgatgg gtcagcgtgg tcgtgagggt ccgatgggac cgcgtggtga ggctggtagc   420
cctggtccga aggagatat gggtagcccg ggtccgaaag gtgaccgtgg ttttcctggt   480
acaccgggta ttccagggcc tctgggtcat cctggtcctc agggtccgaa aggtcagaaa   540
gggagtgtgg gagatccggg tatggagggt ccgatggggc agcgcggtcg tgaaggtccg   600
atgggcccgc gtggtgaagc c                                            621

<210> SEQ ID NO 6
<211> LENGTH: 189
<212> TYPE: PRT
<213> ORGANISM: Artificial Sequence
<220> FEATURE:
<223> OTHER INFORMATION: C17B3

<400> SEQUENCE: 6

Gly Leu Gln Gly Leu Arg Gly Glu Val Gly Leu Pro Gly Val Lys Gly
1               5                  10                  15

Asp Lys Gly Pro Met Gly Pro Pro Gly Pro Lys Gly Asp Gln Gly Glu

```
            20                  25                  30
Lys Gly Pro Arg Gly Leu Thr Gly Glu Pro Gly Met Arg Gly Leu Pro
             35                  40                  45

Gly Ala Val Gly Glu Pro Gly Ala Lys Gly Ala Met Gly Pro Ala Gly
     50                  55                  60

Leu Gln Gly Leu Arg Gly Glu Val Gly Leu Pro Gly Val Lys Gly Asp
 65                  70                  75                  80

Lys Gly Pro Met Gly Pro Pro Gly Pro Lys Gly Asp Gln Gly Glu Lys
                 85                  90                  95

Gly Pro Arg Gly Leu Thr Gly Glu Pro Gly Met Arg Gly Leu Pro Gly
            100                 105                 110

Ala Val Gly Glu Pro Gly Ala Lys Gly Ala Met Gly Pro Ala Gly Leu
        115                 120                 125

Gln Gly Leu Arg Gly Glu Val Gly Leu Pro Gly Val Lys Gly Asp Lys
    130                 135                 140

Gly Pro Met Gly Pro Pro Gly Pro Lys Gly Asp Gln Gly Glu Lys Gly
145                 150                 155                 160

Pro Arg Gly Leu Thr Gly Glu Pro Gly Met Arg Gly Leu Pro Gly Ala
                165                 170                 175

Val Gly Glu Pro Gly Ala Lys Gly Ala Met Gly Pro Ala
            180                 185
```

<210> SEQ ID NO 7
<211> LENGTH: 567
<212> TYPE: DNA
<213> ORGANISM: Artificial Sequence
<220> FEATURE:
<223> OTHER INFORMATION: C17B3-DNA

<400> SEQUENCE: 7

```
ggtctgcagg gtctgcgtgg tgaagtagga ctgccgggtg tgaaaggaga taaggacca      60
atgggtccac caggaccaaa aggagatcaa ggagaaaaag gaccacgtgg tctgacaggt    120
gaaccgggta tgcgtgggct gccgggagca gttggagaac cggagcaaa aggagcaatg     180
ggtccagcag gactgcaggg tctgcgcggt gaagtgggac tgcctggtgt aaagggggat    240
aaagggccga tgggtccgcc gggtccgaaa ggagatcagg gagaaaaagg ccgcgtggt     300
ctgaccggtg aaccgggaat gcgtggtctg ccggggctg tgggtgagcc aggtgcaaaa     360
ggtgcaatgg gtcctgcagg tctgcaagga ctgcgtggag aagtgggtct gcctggtgtg    420
aaaggtgata aggtccgat gggtcctccg ggtccgaaag gtgatcaggg tgaaaaaggt     480
ccgcgtggtc tgacgggtga accgggcatg cgtggtctgc tggggcagt tggtgaaccg     540
ggggcaaaag gtgctatggg gccggca                                         567
```

<210> SEQ ID NO 8
<211> LENGTH: 357
<212> TYPE: DNA
<213> ORGANISM: Artificial Sequence
<220> FEATURE:
<223> OTHER INFORMATION: C17C1-DNA

<400> SEQUENCE: 8

```
ggtgcagatt ttgcaggtga tctggattat aatgaactgg cagttcgtgt tagcgaaagc      60
atgcagcgtc agggactgct gcagggaatg gcatataccg ttcagggtcc gccgggtcag    120
ccgggtcctc aaggtcctcc tggtattagc aaagttttta gtgcatattc aaacgtgacg    180
gcagatctga tggatttttt tcagacgtat ggtgcaattc agggtcctcc tgggcaaaaa    240
```

```
ggtgaaatgg gtacacctgg tccgaaaggc gatcgtggtc cggccggtcc gccgggccac    300
cctggtcctc ctggccctcg tggtcataaa ggtgagaaag gtgataaagg tgatcaa       357
```

<210> SEQ ID NO 9
<211> LENGTH: 1497
<212> TYPE: PRT
<213> ORGANISM: Artificial Sequence
<220> FEATURE:
<223> OTHER INFORMATION: COL17A1

<400> SEQUENCE: 9

```
Met Asp Val Thr Lys Lys Asn Lys Arg Asp Gly Thr Glu Val Thr Glu
1               5                   10                  15

Arg Ile Val Thr Glu Thr Val Thr Thr Arg Leu Thr Ser Leu Pro Pro
            20                  25                  30

Lys Gly Gly Thr Ser Asn Gly Tyr Ala Lys Thr Ala Ser Leu Gly Gly
        35                  40                  45

Gly Ser Arg Leu Glu Lys Gln Ser Leu Thr His Gly Ser Ser Gly Tyr
    50                  55                  60

Ile Asn Ser Thr Gly Ser Thr Arg Gly His Ala Ser Thr Ser Ser Tyr
65                  70                  75                  80

Arg Arg Ala His Ser Pro Ala Ser Thr Leu Pro Asn Ser Pro Gly Ser
                85                  90                  95

Thr Phe Glu Arg Lys Thr His Val Thr Arg His Ala Tyr Glu Gly Ser
            100                 105                 110

Ser Ser Gly Asn Ser Ser Pro Glu Tyr Pro Arg Lys Glu Phe Ala Ser
        115                 120                 125

Ser Ser Thr Arg Gly Arg Ser Gln Thr Arg Glu Ser Glu Ile Arg Val
    130                 135                 140

Arg Leu Gln Ser Ala Ser Pro Ser Thr Arg Trp Thr Glu Leu Asp Asp
145                 150                 155                 160

Val Lys Arg Leu Leu Lys Gly Ser Arg Ser Ala Ser Val Ser Pro Thr
                165                 170                 175

Arg Asn Ser Ser Asn Thr Leu Pro Ile Pro Lys Lys Gly Thr Val Glu
            180                 185                 190

Thr Lys Ile Val Thr Ala Ser Ser Gln Ser Val Ser Gly Thr Tyr Asp
        195                 200                 205

Ala Thr Ile Leu Asp Ala Asn Leu Pro Ser His Val Trp Ser Ser Thr
    210                 215                 220

Leu Pro Ala Gly Ser Ser Met Gly Thr Tyr His Asn Asn Met Thr Thr
225                 230                 235                 240

Gln Ser Ser Ser Leu Leu Asn Thr Asn Ala Tyr Ser Ala Gly Ser Val
                245                 250                 255

Phe Gly Val Pro Asn Asn Met Ala Ser Cys Ser Pro Thr Leu His Pro
            260                 265                 270

Gly Leu Ser Thr Ser Ser Ser Val Phe Gly Met Gln Asn Asn Leu Ala
        275                 280                 285

Pro Ser Leu Thr Thr Leu Ser His Gly Thr Thr Thr Ser Thr Ala
    290                 295                 300

Tyr Gly Val Lys Lys Asn Met Pro Gln Ser Pro Ala Ala Val Asn Thr
305                 310                 315                 320

Gly Val Ser Thr Ser Ala Ala Cys Thr Thr Ser Val Gln Ser Asp Asp
                325                 330                 335

Leu Leu His Lys Asp Cys Lys Phe Leu Ile Leu Glu Lys Asp Asn Thr
```

```
                340             345             350
Pro Ala Lys Lys Glu Met Glu Leu Leu Ile Met Thr Lys Asp Ser Gly
            355             360             365

Lys Val Phe Thr Ala Ser Pro Ala Ser Ile Ala Ala Thr Ser Phe Ser
            370             375             380

Glu Asp Thr Leu Lys Glu Lys Gln Ala Ala Tyr Asn Ala Asp Ser
385             390             395             400

Gly Leu Lys Ala Glu Ala Asn Gly Asp Leu Lys Thr Val Ser Thr Lys
            405             410             415

Gly Lys Thr Thr Thr Ala Asp Ile His Ser Tyr Gly Ser Ser Gly
            420             425             430

Gly Gly Ser Gly Gly Gly Gly Val Gly Ala Gly Gly Gly Pro
            435             440             445

Trp Gly Pro Ala Pro Ala Trp Cys Pro Cys Gly Ser Cys Cys Ser Trp
            450             455             460

Trp Lys Trp Leu Leu Gly Leu Leu Thr Trp Leu Leu Leu Gly
465             470             475             480

Leu Leu Phe Gly Leu Ile Ala Leu Ala Glu Glu Val Arg Lys Leu Lys
            485             490             495

Ala Arg Val Asp Glu Leu Glu Arg Ile Arg Arg Ser Ile Leu Pro Tyr
            500             505             510

Gly Asp Ser Met Asp Arg Ile Glu Lys Asp Arg Leu Gln Gly Met Ala
            515             520             525

Pro Ala Ala Gly Ala Asp Leu Asp Lys Ile Gly Leu His Ser Asp Ser
            530             535             540

Gln Glu Glu Leu Trp Met Phe Val Arg Lys Lys Leu Met Met Glu Gln
545             550             555             560

Glu Asn Gly Asn Leu Arg Gly Ser Pro Gly Pro Lys Gly Asp Met Gly
            565             570             575

Ser Pro Gly Pro Lys Gly Asp Arg Gly Phe Pro Gly Thr Pro Gly Ile
            580             585             590

Pro Gly Pro Leu Gly His Pro Gly Pro Gln Gly Pro Lys Gly Gln Lys
            595             600             605

Gly Ser Val Gly Asp Pro Gly Met Glu Gly Pro Met Gly Gln Arg Gly
            610             615             620

Arg Glu Gly Pro Met Gly Pro Arg Gly Glu Ala Gly Pro Pro Gly Ser
625             630             635             640

Gly Glu Lys Gly Glu Arg Gly Ala Ala Gly Glu Pro Gly Pro His Gly
            645             650             655

Pro Pro Gly Val Pro Gly Ser Val Gly Pro Lys Gly Ser Ser Gly Ser
            660             665             670

Pro Gly Pro Gln Gly Pro Pro Gly Pro Val Gly Leu Gln Gly Leu Arg
            675             680             685

Gly Glu Val Gly Leu Pro Gly Val Lys Gly Asp Lys Gly Pro Met Gly
            690             695             700

Pro Pro Gly Pro Lys Gly Asp Gln Gly Glu Lys Gly Pro Arg Gly Leu
705             710             715             720

Thr Gly Glu Pro Gly Met Arg Gly Leu Pro Gly Ala Val Gly Glu Pro
            725             730             735

Gly Ala Lys Gly Ala Met Gly Pro Ala Gly Pro Asp Gly His Gln Gly
            740             745             750

Pro Arg Gly Glu Gln Gly Leu Thr Gly Met Pro Gly Ile Arg Gly Pro
            755             760             765
```

```
Pro Gly Pro Ser Gly Asp Pro Gly Lys Pro Gly Leu Thr Gly Pro Gln
        770                 775                 780

Gly Pro Gln Gly Leu Pro Gly Thr Pro Gly Arg Pro Gly Ile Lys Gly
785                 790                 795                 800

Glu Pro Gly Ala Pro Gly Lys Ile Val Thr Ser Glu Gly Ser Ser Met
                805                 810                 815

Leu Thr Val Pro Gly Pro Pro Gly Pro Pro Gly Ala Met Gly Pro Pro
                820                 825                 830

Gly Pro Pro Gly Ala Pro Gly Pro Ala Gly Pro Ala Gly Leu Pro Gly
            835                 840                 845

His Gln Glu Val Leu Asn Leu Gln Gly Pro Pro Gly Pro Pro Gly Pro
        850                 855                 860

Arg Gly Pro Pro Gly Pro Ser Ile Pro Gly Pro Pro Gly Pro Arg Gly
865                 870                 875                 880

Pro Pro Gly Glu Gly Leu Pro Gly Pro Pro Gly Pro Pro Gly Ser Phe
                885                 890                 895

Leu Ser Asn Ser Glu Thr Phe Leu Ser Gly Pro Pro Gly Pro Pro Gly
            900                 905                 910

Pro Pro Gly Pro Lys Gly Asp Gln Gly Pro Pro Gly Pro Arg Gly His
            915                 920                 925

Gln Gly Glu Gln Gly Leu Pro Gly Phe Ser Thr Ser Gly Ser Ser Ser
930                 935                 940

Phe Gly Leu Asn Leu Gln Gly Pro Pro Gly Pro Pro Gly Pro Gln Gly
945                 950                 955                 960

Pro Lys Gly Asp Lys Gly Asp Pro Gly Val Pro Gly Ala Leu Gly Ile
                965                 970                 975

Pro Ser Gly Pro Ser Glu Gly Gly Ser Ser Thr Met Tyr Val Ser
            980                 985                 990

Gly Pro Pro Gly Pro Pro Gly Pro Pro Gly Pro Pro Gly Ser Ile Ser
            995                1000                1005

Ser Ser Gly Gln Glu Ile Gln Gln Tyr Ile Ser Glu Tyr Met Gln
    1010                1015                1020

Ser Asp Ser Ile Arg Ser Tyr Leu Ser Gly Val Gln Gly Pro Pro
    1025                1030                1035

Gly Pro Pro Gly Pro Pro Gly Pro Val Thr Thr Ile Thr Gly Glu
    1040                1045                1050

Thr Phe Asp Tyr Ser Glu Leu Ala Ser His Val Val Ser Tyr Leu
    1055                1060                1065

Arg Thr Ser Gly Tyr Gly Val Ser Leu Phe Ser Ser Ile Ser
    1070                1075                1080

Ser Glu Asp Ile Leu Ala Val Leu Gln Arg Asp Asp Val Arg Gln
    1085                1090                1095

Tyr Leu Arg Gln Tyr Leu Met Gly Pro Arg Gly Pro Pro Gly Pro
    1100                1105                1110

Pro Gly Ala Ser Gly Asp Gly Ser Leu Leu Ser Leu Asp Tyr Ala
    1115                1120                1125

Glu Leu Ser Ser Arg Ile Leu Ser Tyr Met Ser Ser Ser Gly Ile
    1130                1135                1140

Ser Ile Gly Leu Pro Gly Pro Pro Gly Pro Pro Gly Leu Pro Gly
    1145                1150                1155

Thr Ser Tyr Glu Glu Leu Leu Ser Leu Leu Arg Gly Ser Glu Phe
    1160                1165                1170
```

-continued

```
Arg Gly Ile Val Gly Pro Pro Gly Pro Pro Gly Pro Pro Gly Ile
1175                1180                1185

Pro Gly Asn Val Trp Ser Ser Ile Ser Val Glu Asp Leu Ser Ser
1190                1195                1200

Tyr Leu His Thr Ala Gly Leu Ser Phe Ile Pro Gly Pro Pro Gly
1205                1210                1215

Pro Pro Gly Pro Pro Gly Pro Arg Gly Pro Pro Gly Val Ser Gly
1220                1225                1230

Ala Leu Ala Thr Tyr Ala Ala Glu Asn Ser Asp Ser Phe Arg Ser
1235                1240                1245

Glu Leu Ile Ser Tyr Leu Thr Ser Pro Asp Val Arg Ser Phe Ile
1250                1255                1260

Val Gly Pro Pro Gly Pro Pro Gly Pro Gln Gly Pro Pro Gly Asp
1265                1270                1275

Ser Arg Leu Leu Ser Thr Asp Ala Ser His Ser Arg Gly Ser Ser
1280                1285                1290

Ser Ser Ser His Ser Ser Ser Val Arg Arg Gly Ser Ser Tyr Ser
1295                1300                1305

Ser Ser Met Ser Thr Gly Gly Gly Gly Ala Gly Ser Leu Gly Ala
1310                1315                1320

Gly Gly Ala Phe Gly Glu Ala Ala Gly Asp Arg Gly Pro Tyr Gly
1325                1330                1335

Thr Asp Ile Gly Pro Gly Gly Gly Tyr Gly Ala Ala Ala Glu Gly
1340                1345                1350

Gly Met Tyr Ala Gly Asn Gly Gly Leu Leu Gly Ala Asp Phe Ala
1355                1360                1365

Gly Asp Leu Asp Tyr Asn Glu Leu Ala Val Arg Val Ser Glu Ser
1370                1375                1380

Met Gln Arg Gln Gly Leu Leu Gln Gly Met Ala Tyr Thr Val Gln
1385                1390                1395

Gly Pro Pro Gly Gln Pro Gly Pro Gln Gly Pro Pro Gly Ile Ser
1400                1405                1410

Lys Val Phe Ser Ala Tyr Ser Asn Val Thr Ala Asp Leu Met Asp
1415                1420                1425

Phe Phe Gln Thr Tyr Gly Ala Ile Gln Gly Pro Pro Gly Gln Lys
1430                1435                1440

Gly Glu Met Gly Thr Pro Gly Pro Lys Gly Asp Arg Gly Pro Ala
1445                1450                1455

Gly Pro Pro Gly His Pro Gly Pro Pro Gly Pro Arg Gly His Lys
1460                1465                1470

Gly Glu Lys Gly Asp Lys Gly Asp Gln Val Tyr Ala Gly Arg Arg
1475                1480                1485

Arg Arg Arg Ser Ile Ala Val Lys Pro
1490                1495
```

US 12,043,657 B2

HUMAN COLLAGEN 17-TYPE POLYPEPTIDE, PRODUCTION METHOD THEREFOR AND USE THEREOF

This application is a 371 (National Stage) of PCT/CN2020/123600 filed Oct. 26, 2020 and claims foreign priority to Chinese Patent Application No. 201911051106.3 filed Oct. 31, 2019, the disclosed contents of which are hereby incorporated by reference in the entirety.

REFERENCE TO A SEQUENCE LISTING

This application contains a Sequence Listing in computer readable form. The computer readable form is incorporated herein by reference.

TECHNICAL FIELD

The present invention belongs to the technical field of genetic engineering, and relates to polypeptides, production methods and uses thereof.

BACKGROUND ART

Collagen

Collagen is generally white, transparent, and unbranched fibrils, which is the basic support for skin and bones. It can account for 25% to 35% of the total amount of protein. Collagen is mainly distributed in the skin, blood vessels, bones, tendons, teeth and cartilage among other parts of the human body, serving as the main matrix and scaffolds of these tissues, and it protects and connects various tissues, and plays important physiological functions in the body. Therefore, collagen can be widely utilized in industries such as medicine and cosmetics.

The collagen products currently on the market are all taken from tissues of animals such as pigs, bovines, and fish. Although the collagen of certain animals is highly similar to that of humans, it is still difficult to avoid the risk of viral infection and sensitization. At present, a small amount of animal-derived collagen has been used in cosmetics, but it is difficult to be widely used in medical equipment or sophisticated tissue engineering products to perform the original biological function of collagen. Moreover, collagen prepared by conventional methods generally has a strong coagulation function, which leads to a great risk of thrombosis when it is used in certain tissue engineering products, thereby greatly limiting its extensive and in-depth application.

The traditional method of producing collagen is to process animal-derived tissues by utilizing acid, alkali, and enzymatic hydrolysis to extract collagen derivatives. The collagen extracted by these methods has lost its original biological activity and cannot be used in the field of biomedicine to perform its real function. Some research institutions in China and abroad express human-derived collagen in vitro through conventional recombinant expression methods, but the production cost is usually too high and the production cycle is too long to be put into large-scale production. Therefore, there is an urgent need in the market for a collagen material with excellent biomaterial properties, a high degree of amino acid sequence homology with the human body, and which can be prepared in large quantities in an industrialized system.

Type 17 Human Collagen

From a structural point of view, the structure of natural collagen in the human body is very complicated, which makes it extremely difficult to express and prepare in large quantities human-derived collagen by conventional means. The most common structural feature of collagen is a triple helix structure formed by three peptide chains, that is, three A peptide chains form a protein in a right-handed super-coiled manner, and such a triple helix region is called a collagen region. Each A peptide chain in molecular structure is composed of repetitive Gly-X-Y (X and Y represent any amino acid residues other than Gly, X is often Pro, and Y is often Hyp) peptide fragments that form a left-handed helix, and under the interaction of amino acid residues, 3 A peptide chains are centered on the same axis and form a stable triple helix structure in a right-handed supercoiled manner. Therefore, it is generally difficult for collagen sequences to spontaneously combine to form a stable triple helix structure in order to perform biological functions. Such difficulties severely hinder the development and production of human collagen.

The human body contains 28 different types of collagen, which are divided into common fibrous collagen and uncommon non-fibrous collagen. Type I, Type II and Type III in human skin belong to fibrous collagen. Among non-fibrous collagen, a very important subtype of collagen is type 17 collagen, collagen XVII, (encoded by the COL17A1 gene in the human body). Type 17 collagen is a homotrimer formed by the combination of three COL17A1 chains, with a single chain molecular weight of 180 kDa. It comprises a spherical intracellular domain of 70 kDa, a transmembrane domain and an extracellular collagen domain of 120 kDa, which has robust thermal stability. Recent studies have confirmed that type 17 collagen is an important component of hemidesmosome in epidermal stem cells in the human body and plays an important role in both cell aging and skin differentiation. However, humans currently have very limited understanding of the structure and function of non-fibrous collagen, especially for type 17 collagen.

The inventor has studied the structure and function of collagen in depth for many years. In particular, for the first time in the world, he analyzed the new atomic structure of multiple segments of human collagen, and posted it to the international protein structure database for public display, and accumulated rich research experience. Through repeated explorations, the inventor has successfully achieved the recombinant expression of several extracellular functional regions of type 17 collagen, and found that it has excellent biomaterial properties, its preparation method is simple, easy to expand production, and can be widely used in industries such as medicine and cosmetics.

SUMMARY OF THE INVENTION

The present invention is based in part on the following findings:

The polypeptides C17A3, C17B3 and C17C1 of the present invention have comparable or greater cell adhesion effects compared with existing human collagen, and the polypeptides C17A3, C17B3 and C17C1 exist in water-soluble form after being expressed in host cells, and the preparation method is simple, easy to expand production.

Against the drawbacks of the prior art shown in the background art, the present invention provides:

Item 1. A polypeptide comprising 63-1496 continuous amino acid residues in SEQ ID No. 9, wherein the polypeptide has cell adhesion activity.

Item 2. A polypeptide, wherein the polypeptide comprises or consists of the sequence shown in $(A)_m$, wherein each A is selected from the amino acid sequence shown in any one of SEQ ID No. 1, SEQ ID No. 2 and SEQ ID No. 3, or the amino acid sequence with one or more, such as 2, 3, 4 or 5 amino acid residues substituted, added, or deleted in any one of SEQ ID No. 1, SEQ ID No. 2 and SEQ ID No. 3, or the sequence with a sequence identity of 83%, 84%, 85%, 86%, 87%, 88%, 89%, 90%, 91%, 92%, 93%, 94%, 95%, 96% or 97% to the amino acid sequence shown in any one of SEQ ID No. 1, SEQ ID No. 2 and SEQ ID No. 3; m is an integer between 1-10, wherein each A is the same or different and adjacent two As are directly linked by a peptide bond or linked by more than one amino acid residues; wherein the polypeptide has cell adhesion activity. The interval described herein includes endpoints, for example, between 1 to 10 includes 1, 2, 3, 4, 5, 6, 7, 8, 9, 10, that is, m can be 1, 2, 3, 4, 5, 6, 7, 8, 9 or 10.

Item 3. The polypeptide of Item 1 or 2, wherein the polypeptide comprises or consists of the amino acid sequence shown in SEQ ID No. 1, SEQ ID No. 2, SEQ ID No. 3, SEQ ID No. 4, or SEQ ID No. 6.

Item 4. A polynucleotide encoding the polypeptide according to any one of Items 1-3, preferably, the polynucleotide comprising or consisting of nucleotide sequence shown in SEQ ID No. 5, SEQ ID No. 7, or SEQ ID No. 8.

Item 5. An expression vector comprising the polynucleotide according to Item 4.

Item 6. A host cell comprising the expression vector according to Item 5 or expressing the polypeptide according to any one of Items 1-3, wherein the host cell is preferably an *Escherichia coli* (*E. coli*) cell.

Item 7. A method for preparing the polypeptide according to any one of Items 1-3, which comprises:
(1) culturing the host cell according to Item 6 in a production medium;
(2) isolating the polypeptide according to any one of Items 1-3 from the host cell.

Item 8. A composition comprising the polypeptide according to any one of Items 1-3 or the polypeptide prepared according to the method of Item 7.

Item 9. A article comprising the polypeptide according to any one of Items 1-3 or the polypeptide prepared according to the method of Item 7 or the composition according to Item 8, wherein the article is a pharmaceutical composition, a medical device, a tissue engineering product, cosmetics, or a health product, preferably the pharmaceutical composition is a topical preparation, preferably a topical smear preparation, such as a topical gel or a topical infiltration preparation; wherein preferably the topical gel further comprises pharmaceutically acceptable carriers, and the topical infiltration preparation further comprises sterile medical cotton balls.

Item 10. Use of the polypeptide according to any one of Items 1-3 or the polypeptide prepared by the method of Item 7, the polynucleotide of Item 4, the expression vector of Item 5, the host cell of Item 6, or the composition of Item 8 in the preparation of articles, preferably medical devices, tissue engineering products, cosmetics, and health products.

Compared with the prior art, the present invention has the following characteristics:
(1) The type 17 human collagen sequence selected for the first time in the present invention is a sequence optimized for long-term screening;
(2) The *E. coli* expression system is employed, which is suitable for large-scale amplification, and one round of fermentation can be completed in 20 hours. The production cost is very low. Due to the codon optimization of *E. coli* for the gene sequence and the selection of 2×YT medium, the output is in tremendous amount;
(3) The recombinant human-derived collagen produced has very good hydrophilicity and stability, and its amino acid composition is 100% identical to the corresponding part of the amino acid sequence of natural collagen. It will not cause immune rejection and allergic reaction when applied to the human body, and can be widely used in biomedicine and cosmetics industry;
(4) The product of the present invention has undergone activity detection and has a biological activity that can reach or exceed the biological activity of natural protein in the human body, which can exercise the function of the natural protein in the human body to achieve the purpose of real product application;
(5) The technical design of the present invention can effectively reduce the risk of coagulation of collagen when used in the human body, while retaining the high cell adhesion activity of collagen, and has a wide range of tissue engineering application prospects.

DETAILED EMBODIMENTS

Figure 1:
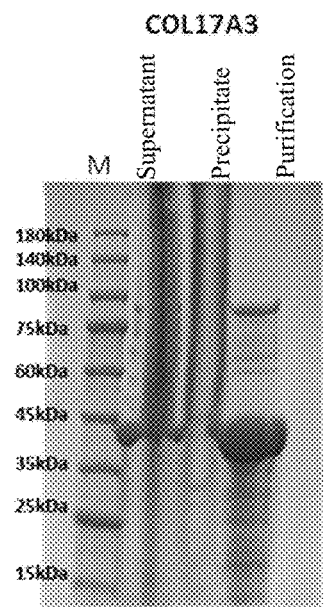
FIG. 1 is a protein electrophoresis diagram obtained after expression and purification of the Trx-C17A3 protein of the present invention; the molecular weight of the Trx-C17A3 protein detected by electrophoresis is about 42 kDa.

A further description is provided below to facilitate the understanding of the present invention.

As used herein, "medical devices" refer to instruments, equipment, appliances, in vitro diagnostic reagents and calibrators, materials, and other similar or related items used directly or indirectly on the human body.

As used herein, "tissue engineering products" refer to products used for tissue engineering. Tissue engineering is an emerging discipline that combines cell biology and material science to construct tissues or organs in vitro or in vivo.

As used herein, "isolation" refers to isolating target polypeptides from cultured host cells, for example, to disrupt the host cells and purify the target polypeptides. In the case that the purified target polypeptides have purification tags, such as Trx or His tag, "insolation" also includes the removal of the Trx or His tag by restriction digestion.

"Pharmaceutically acceptable carriers" are well known to those skilled in the art, and those skilled in the art can select pharmaceutically acceptable carriers suitable for use in the compositions or articles of the present invention. For example, pharmaceutically acceptable carriers include, but are not limited to: buffers such as phosphoric acid, citric acid and other organic acids; antioxidants, including ascorbic acid and methionine; preservatives (such as octadecyl dimethyl benzyl ammonium chloride; hexamethonium chloride; benzalkonium chloride; benzethonium chloride; phenol, butanol or benzyl alcohol; alkyl parabens such as methyl paraben or propyl paraben; catechol; resorcine; cyclohexanol; 3-pentanol; and m-cresol); low molecular weight (less than about 10 residues) polypeptides; proteins, such as serum albumin, gelatin, or immunoglobulin; hydrophilic polymers such as polyvinylpyrrolidone; amino acids such as glycine, glutamine, asparagine, histidine, arginine or lysine; monosaccharides, disaccharides, and other carbohydrates, including glucose, mannose or dextrin; chelating agents such as EDTA; sugars such as sucrose, mannitol, trehalose, or sorbitol; salt-forming counterions such as sodium; metal complexes (such as Zn-protein complexes); and/or non-ionic surfactants such as polyethylene glycol (PEG).

In the present invention, the sequence of human type 17 collagen COL17A1 is selected for screening and optimization. The sequence of the human collagen a type 17 is the NCBI reference sequence: Q9UMD9.3 (SEQ ID No. 9).

(SEQ ID No. 9)
MDVTKKNKRDGTEVTERIVTETVTTRLTSLPPKGGTSNGYAKTASLGGGS

RLEKQSLTHGSSGYINSTGSTRGHASTSSYRRAHSPASTLPNSPGSTFER

KTHVTRHAYEGSSSGNSSPEYPRKEFASSSTRGRSQTRESEIRVRLQSAS

PSTRWTELDDVKRLLKGSRSASVSPTRNSSNTLPIPKKGTVETKIVTASS

QSVSGTYDATILDANLPSHVWSSTLPAGSSMGTTTQSSSLLNTNAYSAGS

VFGVPNNMASCSPTLHPGLSTSSSVFGMQNNLAPSLTTLSHGTTTTSTAY

GVKKNMPQSPAAVNTGVSTSAACTTSVQSDDLLHKDCKFLILEKDNTPAK

KEMELLIMTKDSGKVFTASPASIAATSFSEDTLKKEKQAAYNADSGLKAE

ANGDLKTVSTKGKTTTADIHSYGSSGGGSGGGGVGGAGGGPWGPAPAW

CPCGSCCSWWKWLLGLLLTWLLLLGLLFGLIALAEEVRKLKARVDELERI

RRSILPYGDSMDRIEKDRLQGMAPAAGADLDKIGLHSDSQEELWMFVRKK

LMMEQENGNLRGSPGPKGDMGSPGPKGDRGFPGTPGIPGPLGHPGPQGPK

GQKGSVGDPGMEGPMGQRGREGPMGPRGEAGPPGSGEKGERGAAGEPGPH

GPPGVPGSVGPKGSSGSPGPQGPPGPVGLQGLRGEVGLPGVKGDKPMGP

PGPKGDQGEKGPRGLTGEPGMRGLPGAVGEPGAKGAMGPAGPDGHQGPRG

EQGLTGMPGIRGPPGPSGDPGKPGLTGPQGPQGLPGTPGRPGIKGEPGAP

GKIVTSEGSSMLTVPGPPGPPGAMGPPGPPGAPGPAGPAGLPGHQEVLNL

QGPPGPPGPRGPPGPSIPGPPGPRGPPGEGLPGPPGPPGSFLSNSETFLS

GPPGPPGPPGPKGDQGPPGPRGHQGEQGLPGFSTSGSSSFGLNLQGPPGP

PGPQGPKGDKGDPGVPGALGIPSGPSEGGSSSTMYVSGPPGPPGPPGPPG

SISSSGQEIQQYISEYMQSDSIRSYLSGVQGPPGPPGPPGPVTTITGETF

DYSELASHVVSYLRTSGYGVSLFSSSISSEDILAVLQRDDVRQYLRQYLM

GPRGPPGPPGASGDGSLLSLDYAELSSRILSYMSSSGISIGLPGPPGPPG

LPGTSYEELLSLLRGSEFRGIVGPPGPPGPPGIPGNVWSSISVEDLSSYL

HTAGLSFIPGPPGPPGPPGPRGPPGVSGALATYAAENSDSFRSELISYLT

SPDVRSFIVGPPGPPGPQGPPGDSRLLSTDASHSRGSSSSSHSSSVRRGS

SYSSSMSTGGGGAGSLGAGGAFGEAAGDRGPYGTDIGPGGGYGAAAEGGM

YAGNGGLLGADFAGDLDYNELAVRVSESMQRQGLLQGMAYTVQGPPGQPG

PQGPPGISKVFSAYSNVTADLMDFFQTYGAIQGPPGQKGEMGTPGPKGDR

GPAGPPGHPGPPGPRGHKGEKGDKGDQVYAGRRRRRSIAVKP

The bold underlined part in the sequence described above is the amino acid sequence selected in the present invention. The applicant found through a lot of research that the selected sequence described above has strong water solubility, high recombinant expression yield, simple purification process, and achieves better cell adhesion than commercial human collagen or other sequences in SEQ ID No. 9, with a variety of excellent biological material properties. In the present invention, the polypeptide is not the full-length sequence of SEQ ID No. 9.

The present invention is based in part on the following findings: a polypeptide comprising at least 63 continuous amino acid residues in SEQ ID No. 9 can have better biomaterial properties than commercial human collagen, as demonstrated in the examples. Those skilled in the art can appropriately select the continuous amino acid residues constituting the recombinant collagen. For example, the length of continuous amino acid residues may be 48-100, 50-72, 54-57 and 48-72 among others.

In the present invention, the sequences of several specific amino acid regions have been detected:

(1) C17A:
(SEQ ID No. 1)
GSPGPKGDMGSPGPKGDRGFPGTPGIPGPLGHPGPQGPKGQKGSVGDPGM

EGPMGQRGREGPMGPRGEA;

(2) C17B:
(SEQ ID No. 2)
GLQGLRGEVGLPGVKGDKGPMGPPGPKGDQGEKGPRGLTGEPGMRGLPGA

VGEPGAKGAMGPA;

(3) C17C:
(SEQ ID No. 3)
GADFAGDLDYNELAVRVSESMQRQGLLQGMAYTVQGPPGQPGPQGPPGIS

KVFSAYSNVTADLMDFFQTYGAIQGPPGQKGEMGTPGPKGDRGPAGPPGH

PGPPGPRGHKGEKGDKGDQ;

The polypeptide herein can be recombinant human-derived collagen C17A3, which is a triple repeat sequence of C17A, including 207 amino acids, and the basic repeat unit is:
GSPGPKGDMGSPGPKGDRGFPGTPGIPGPLGHPGPQGPKGQKGSVGDPG MEGPMGQRGREGPMGPRGEA (SEQ ID No. 1), which is human collagen type 17 peptide fragment.
The amino acid sequence of C17A3 is as follows:

(SEQ ID No. 4)
GSPGPKGDMGSPGPKGDRGFPGTPGIPGPLGHPGPQGPKGQKGSVGDPGM

EGPMGQRGREGPMGPRGEAGSPGPKGDMGSPGPKGDRGFPGTPGIPGPLG

HPGPQGPKGQKGSVGDPGMEGPMGQRGREGPMGPRGEAGSPGPKGDMGSP

GPKGDRGFPGTPGIPGPLGHPGPQGPKGQKGSVGDPGMEGPMGQRGREGP

MGPRGEA.

The DNA sequence of C17A3 is as follows:

(SEQ ID No. 5)
GGTAGCCCAGGTCCAAAAGGTGATATGGGAAGCCCAGGTCCGAAAGGTGA

TCGTGGTTTTCCGGGTACACCAGGTATTCCGGGTCCACTGGGTCATCCAG

GTCCGCAAGGTCCGAAAGGCCAGAAAGGTAGCGTGGGTGATCCGGGTATG

GAAGGGCCTATGGGCAGCGTGGGCGTGAAGGGCCGATGGGTCCGCGTGG

TGAAGCAGGTAGCCCGGGGCCTAAAGGGGATATGGGGAGTCCGGGTCCGA

AAGGGGATCGTGGATTTCCGGGTACGCCGGGTATCCCGGGTCCGCTGGGT

CATCCGGGTCCGCAAGGGCCTAAAGGTCAGAAAGGTAGTGTGGGTGATCC

TGGTATGGAAGGTCCGATGGGTCAGCGTGGTCGTGAGGGTCCGATGGGAC

CGCGTGGTGAGGCTGGTAGCCCTGGTCCGAAAGGAGATATGGGTAGCCCG

GGTCCGAAAGGTGACCGTGGTTTTCCTGGTACACCGGGTATTCCAGGGCC

TCTGGGTCATCCTGGTCCTCAGGGTCCGAAAGGTCAGAAAGGGAGTGTGG

GAGATCCGGGTATGGAGGGTCCGATGGGGCAGCGCGGTCGTGAAGGTCCG

ATGGGCCCGCGTGGTGAAGCC.

The polypeptide herein may be human-derived collagen C17B3, which is a triple repeat sequence of C17B, including 189 amino acids, and the basic repeat unit is:
GLQGLRGEVGLPGVKGDKGPMGPPGPKGDQG-EKGPRGLTGEPGMRGLP GAVGEPGAKGAMGPA (SEQ ID No. 2), which is human collagen type 17 peptide fragment.
The amino acid sequence of C17B3 is as follows:

(SEQ ID No. 6)
GLQGLRGEVGLPGVKGDKGPMGPPGPKGDQGEKGPRGLTGEPGMRGLPGA

VGEPGAKGAMGPAGLQGLRGEVGLPGVKGDKGPMGPPGPKGDQGEKGPRG

LTGEPGMRGLPGAVGEPGAKGAMGPAGLQGLRGEVGLPGVKGDKGPMGPP

GPKGDQGEKGPRGLTGEPGMRGLPGAVGEPGAKGAMGPA.

The DNA sequence of C17B3 is as follows:

(SEQ ID No. 7)
GGTCTGCAGGGTCTGCGTGGTGAAGTAGGACTGCCGGGTGTGAAAGGAGA

TAAAGGACCAATGGGTCCACCAGGACCAAAAGGAGATCAAGGAGAAAAAG

GACCACGTGGTCTGACAGGTGAACCGGGTATGCGTGGGCTGCCGGGAGCA

GTTGGAGAACCGGGAGCAAAAGGAGCAATGGGTCCAGCAGGACTGCAGGG

TCTGCGCGGTGAAGTGGGACTGCCTGGTGTTAAAGGGGATAAAGGGCCGA

TGGGTCCGCCGGGTCCGAAAGGAGATCAGGGAGAAAAAGGGCCGCGTGGT

CTGACCGGTGAACCGGGAATGCGTGGTCTGCCGGGGGCTGTGGGTGAGCC

AGGTGCAAAAGGTGCAATGGGTCCTGCAGGTCTGCAAGGACTGCGTGGAG

AAGTGGGTCTGCCTGGTGTGAAAGGTGATAAAGGTCCGATGGGTCCTCCG

GGTCCGAAAGGTGATCAGGGTGAAAAAGGTCCGCGTGGTCTGACGGGTGA

ACCGGGCATGCGTGGTCTGCCTGGGGCAGTTGGTGAACCGGGGGCAAAAG

GTGCTATGGGGCCGGCA.

The polypeptide herein can be recombinant human-derived collagen C17C1, which is a repeat sequence of C17C, including 119 amino acids, and the basic repeat unit is:
GADFAGDLDYNELAVRVSESMQRQGLLQGMAY-TVQGPPGQPGPQGPPGI SKVFSAYSNVTADLMD-FFQTYGAIQGPPGQKGEMGTPGPKGDRGPAGPP GHPGPPGPRGHKGEKGDKGDQ (SEQ ID No. 3), which is the human collagen type 17 peptide.
The amino acid sequence of C17C1 is as follows:

(SEQ ID No. 3)
GADFAGDLDYNELAVRVSESMQRQGLLQGMAYTVQGPPGQPGPQGPPGIS

KVFSAYSNVTADLMDFFQTYGAIQGPPGQKGEMGTPGPKGDRGPAGPPGH

PGPPGPRGHKGEKGDKGDQ.

The DNA sequence of C17C1 is as follows:

(SEQ ID No. 8)
GGTGCAGATTTTGCAGGTGATCTGGATTATAATGAACTGGCAGTTCGTGT

TAGCGAAAGCATGCAGCGTCAGGGACTGCTGCAGGGAATGGCATATACCG

TTCAGGGTCCGCCGGGTCAGCCGGGTCCTCAAGGTCCTCCTGGTATTAGC

AAAGTTTTTAGTGCATATTCAAACGTGACGGCAGATCTGATGGATTTTTT

TCAGACGTATGGTGCAATTCAGGGTCCTCCTGGGCAAAAAGGTGAAATGG

GTACACCTGGTCCGAAAGGCGATCGTGGTCCGGCCGGTCCGCCGGGCCAC

CCTGGTCCTCCTGGCCCTCGTGGTCATAAAGGTGAGAAAGGTGATAAAGG

TGATCAA.

Herein, the polypeptide may include the amino acid sequence shown in any one of SEQ ID No. 1, SEQ ID No. 2, SEQ ID No. 3, SEQ ID No. 4, SEQ ID No. 6 and SEQ ID NO. 9 with substitutions, additions, deletions or insertions of one or more, preferably 2, 3, 4 or 5 amino acid residues, or amino acid sequence with a sequence identity of 83%, 84%, 85%, 86%, 87%, 88%, 89%, 90%, 91%, 92%, 93%, 94%, 95%, 96% or 97% to the amino acid sequence shown in any one of SEQ ID No. 1, SEQ ID No. 2, SEQ ID No. 3, SEQ ID No. 4, SEQ ID No. 6 and SEQ ID No. 9. The "percentage identity of amino acid sequence" relative to the reference polypeptide sequence is defined as the percentage of amino acid residues in the candidate sequence that are identical to the amino acid residues in the reference polypeptide sequence after gaps are introduced when necessary to obtain the maximum percentage of sequence identity when the candidate sequence is aligned with the reference polypeptide sequence, without any conservative substitutions are considered part of sequence identity. The alignment used to determine the percentage identity of amino acid sequences can be achieved in various ways known to those skilled in the art, for example, using publicly available computer software, such as BLAST, BLAST-2, ALIGN or Megalign (DNASTAR) software. Those skilled in the art can determine suitable parameters for aligning sequences, which includes any algorithms required to achieve maximum alignment over the full length of the sequences being compared.

Amino acid addition refers to adding amino acids to the C- or N-terminus of the amino acid sequences, such as any one of SEQ ID No. 1, SEQ ID No. 2, SEQ ID No. 3, SEQ ID No. 4, SEQ ID No. 6, and SEQ ID NO. 9, provided that the polypeptide has collagen characteristics and cell adhesion activity.

Amino acid substitution refers to replacing a certain amino acid residue in a certain position by another amino acid residue in the amino acid sequences, such as the sequence of any one of SEQ ID No. 1, SEQ ID No. 2, SEQ ID No. 3, SEQ ID No. 4, SEQ ID No. 6, and SEQ ID NO 9, provided that the polypeptide has collagen characteristics and cell adhesion activity.

Amino acid insertion refers to inserting amino acid residues to appropriate positions of the amino acid sequences, such as the sequence of any one of SEQ ID No. 1, SEQ ID No. 2, SEQ ID No. 3, SEQ ID No. 4, SEQ ID No. 6 and SEQ ID NO. 9. The inserted amino acid residues can either be adjacent to each other in whole or in part, or none of the inserted amino acids are adjacent to each other, provided that the polypeptide has collagen characteristics and cell adhesion activity.

Amino acid deletion refers to deleting 1, 2 or more than 3 amino acids from amino acid sequences, such as the sequence of any one of SEQ ID No. 1, SEQ ID No. 2, SEQ ID No. 3, SEQ ID No. 4, SEQ ID No. 6, and SEQ ID NO. 9, provided that the polypeptide has collagen characteristics and cell adhesion activity.

In the present invention, substitutions may be conservative amino acid substitutions, which refer to 3, more preferably 2 amino acids or 1 amino acid replaced by amino acids with similar or comparable properties, as compared with any one of the amino acid sequences of SEQ ID No. 1, SEQ ID No. 2, SEQ ID No. 3, SEQ ID No. 4, SEQ ID No. 6, and SEQ ID NO. 9, to form peptides. These conservative variant peptides can be produced by performing amino acid substitutions according to Table 1.

TABLE 1

Conservative Substitution of Amino Acids

| Original Residue | Representative Substitution | Preferred Substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

All amino acids in the polypeptide sequence herein can be L type amino acids, within which one or more (such as 2-5, 2-4 or 2-3) amino acids can also be replaced with amino acids with D type conformation, artificially modified amino acids, and rare amino acids existed in nature among others, in order to improve the bioavailability, stability, and/or antiviral activity of the polypeptides. Among them, D type amino acids refer to the amino acids corresponding to the L type amino acids that make up proteins; artificially modified amino acids refer to common L type amino acids making up proteins that have been modified by methylation, phosphorylation, etc.; rare amino acids existed in nature include uncommon amino acids that make up proteins, and amino acids that do not make up proteins, such as 5-hydroxylysine, methylhistidine, γ aminobutyric acid, homoserine, etc.

In the present invention, recombining human-derived collagen can be carried out by conventional methods in the art. For example, it can be produced in the following steps: (1) constructing genetically engineered bacteria of E. coli; (2) fermentation culturing the genetically engineered bacteria of E. coli; (3) inducing and expressing the recombinant human-derived collagen; and (4) purifying and optionally restriction digest the recombinant human-derived collagen.

In Step (1), the construction of genetically engineered bacteria of E. coli can be carried out as follows: (1) codon optimizing and splicing recombining DNA fragments in the gene helix region of human-derived type 17 collagen by PCR method to finally obtain target gene fragments; (2) inserting the obtained target gene fragments into PET-32a expression vectors to obtain recombinant expression plasmids; (3) transforming the recombinant expression plasmids into E. coli competent cells BL21 (DE3), and screening to obtain positive genetically engineered bacteria of E. coli.

In Steps (2) and (3), the fermentation culture of the genetically engineered bacteria of E. coli and the induction and expression of recombinant human-derived collagen can be carried out as follows: (1) picking the optimized single colony of the genetically engineered bacteria of E. coli from the LAB plate, placing which in 10 ml of LB medium and culturing at 37° C., 220 rpm for 12-16 hours; (2) amplification culturing the bacterial solution inoculated into 2×YT medium at a ratio of 1:100, and culturing at 37° C. for about 3 hours. When the $OD_{600}$ is 0.4-0.6, adding IPTG at a final concentration of 0.5 mM for induction, culturing at 16° C. for additional 20 hours, and collecting the bacteria by centrifugation.

In Step (4), the purification and restriction digestion of recombinant human-derived collagen polypeptides can be carried out as follows: (1) resuspending the bacteria in phosphate buffer (40 mM $NaH_2PO_3$, 500 mM NaCl, pH 7.8), disrupting ultrasonically, and collecting the supernatant by centrifugation; (2) utilizing NI-NTA affinity column to bind recombinant human-derived collagen, rinsing the impure proteins with 10 mM imidazole prior to adding Tev protease (Tobacco Etch Virus enzyme), digesting on the column at 4° C. for 16 hours, and finally obtaining the target collagen polypeptides.

The host cells may be eukaryotic cells, such as fungi and yeast, or prokaryotic cells, such as Enterobacteriaceae, such as *Escherichia coli*. It should be understood that those skilled in the art can replace the above-mentioned *E. coli* strains with other expression strains as host cells.

EXAMPLES

The following examples are provided to illustrate the invention. Those skilled in the art should understand that the examples are merely illustrative and not restrictive. The present invention is limited solely by the scope of the appended claims.

Example 1: Construction, Expression and Purification of Recombinant Human-Derived Collagen Polypeptides Construction and Expression of C17A3 Gene Expression Vector 1. The full-length gene sequence of human-derived collagen C17A3 used in Example 1 is shown in SEQ ID No. 5. This sequence has been codon optimized for the codons of *E. coli*.

2. The full length of C17A3 gene is 621 bp. According to the optimized C17A3 codon gene sequence SEQ ID No. 5, Beijing Shengyuan Kemeng Gene Biotechnology Co., Ltd. is entrusted to synthesize the gene fragment, and after linking the synthesized C17A3 gene fragment to Tev protease restriction sites, the gene fragment is inserted to the PET32a expression vector (provided by the Institute of Biophysics, Chinese Academy of Sciences) through the Kpn I and Xho I restriction sites. The successfully constructed expression plasmid is transformed into *E. coli* competent cells BL21 (DE3) (Merck Company). The specific process is as follows: 1: taking 1 µl of this plasmid to 100 µl of *E. coli* competent cells BL21 (DE3), and letting it stand on ice for 30 min. 2: heat shocking the mixture in a 42° C. water bath for 90 s, then quickly placing it on ice and letting it stand for 2 min. 3: adding 600 µl of non-resistant LB to the mixture and culturing for 1 hour at 37° C., 220 rpm. 4: taking 200 µl of the bacterial solution and evenly spreading it on the ampicillin resistance-containing LB plate (10 g/L peptone, 5 g/L yeast extract, 10 g/L sodium chloride, 15 g/L agar, 100 µg/ml ampicillin antibiotics). 5: culturing the plate upside down in a 37° C. incubator for about 20 h until growing out clear and visible colonies.

3. Picking a single colony from the transformed LB plate and culturing it in 10 ml LB (containing 100 µg/ml ampicillin antibiotics) medium for 12 h-16 h, then transferring it to 2×YT medium (16 g/L peptone, 10 g/L yeast extract, 5 g/L sodium chloride) at the ratio of 1:100 for amplification culturing, culturing at 37° C., 220 rpm until the $OD_{600}$ of the bacterial solution is 0.4-0.6, adding IPTG (Sigma Company, Cat. No.: I5502-1G) at a final concentration of 0.5 mM for inducing expression. The inducing conditions are 18° C., 180 rpm for 20 h. Finally, collecting the bacteria by centrifugation, and storing at −20° C. or immediately proceeding to the next step of purification.

4. Resuspending (1 L) the bacterial precipitation by using about 50 ml of phosphate buffer (pH 7.8) (40 mM sodium dihydrogen phosphate, 500 mM sodium chloride), and disrupting the bacteria by utilizing a high-pressure bacterium disrupting instrument (SCIENTZ BIO) prior to centrifuging at 13000 rpm for 30 min to fully isolate the soluble protein from the inclusion bodies.

5. Equilibrating the Ni-NTA (Qiagen company, Cat. No.: 30210) affinity column with 5 column volumes of binding buffer (40 mM $NaH_2PO_3$, 500 mM NaCl, pH 7.8). Then adding the protein supernatant and incubating at 4° C. for 0.5-1 h to allow the target recombinant protein fully bind to the column material. Then rinsing the impure proteins with 200 ml of washing buffer containing 10 mM imidazole (10 mM imidazole, 40 mM $NaH_2PO_3$, 500 mM NaCl, pH 7.8) (Sigma Company). If Trx-tagged target protein is needed, an elution buffer (250 mM imidazole, 40 mM $NaH_2PO_3$, 500 mM NaCl, pH 7.8) can be used directly to elute the target protein Trx-C17A3. If the Trx-tagged target protein needs to be removed, an appropriate amount of TEV protease with His tag can be added. After incubating at 4° C. for 16 h, collecting the flow-through fluid, which is the target collagen C17A3 with the carrier protein Trx removed.

6. The anion exchange column can be used for rapid purification of the target protein. Dialyzing the target protein into buffer A (20 mM Tris, 15 mM NaCl, pH 8.0), letting it flow through the anion exchange column Hitrap Q (GE Healthcare), and gradient eluting with buffer B (20 mM Tris, 1 M NaCl, pH 8.0), collecting different elution fractions to detect protein. Dialyzing the obtained target protein product overnight, and lyophilizing it into dry powder for later use.

7. Detecting the molecular weight and purity of the obtained C17A3 protein by SDS-PAGE. The specific process is: taking 40 µl of purified protein solution, adding 10 µl of 5× protein loading buffer (250 mM Tris-HCl (pH: 6.8), 10% SDS, 0.5% bromophenol blue, 50% glycerol, 5% β-mercaptoethanol), boiling in 100° C. boiling water at for 10 min, then adding 10 µl per well to SDS-PAGE protein gel, running at 80V for 2 h, and staining the protein with Coomassie Brilliant Blue Staining Solution (0.1% Coomassie Brilliant Blue R-250, 25% Isopropanol, 10% acetic acid glacial) for 20 min, then utilizing protein decolorizing solution (10% acetic acid, 5% ethanol) for decolorization. Finally, measuring the protein activity in comparison with human natural collagen.

Construction and Expression of C17B3 Gene Expression Vector

1. The full-length gene sequence of human-derived collagen C17B3 used in Example 2 is shown in SEQ ID No. 7. This sequence has been codon optimized for the codons of *E. coli*.

2. The full length of C17B3 gene is 567 bp. According to the optimized C17B3 codon gene sequence SEQ ID No. 7, Beijing Shengyuan Kemeng Gene Biotechnology Co., Ltd. is entrusted to synthesize the gene fragment, and after linking the synthesized C17B3 gene fragment to Tev protease restriction sites, the gene fragment is inserted to the PET32a expression vector (provided by the Institute of Biophysics, Chinese Academy of Sciences) through the Kpn I and Xho I restriction sites. The successfully constructed expression plasmid is transformed into *E. coli* competent cells BL21 (DE3) (Merck Company). The specific process is as follows: 1: taking 1 µl of this plasmid to 100 µl of *E. coli* competent cells BL21 (DE3), and letting it stand on ice for 30 min. 2: heat shocking the mixture in a 42° C. water bath for 90 s, then quickly placing it on ice and letting it stand for 2 min. 3: adding 600 µl of non-resistant LB to the mixture and culturing for 1 hour at 37° C., 220 rpm. 4: taking 200 μl of the bacterial solution and evenly spreading it on the ampicillin resistance-containing LB plate (10 g/L peptone, 5 g/L yeast extract, 10 g/L sodium chloride, 15 g/L agar, 100 μg/ml ampicillin antibiotics). 5: culturing the plate upside down in a 37° C. incubator for about 20 h until growing out clear and visible colonies.

3. Picking a single colony from the transformed LB plate and culturing it in 10 ml LB (containing 100 μg/ml ampicillin antibiotics) medium for 12 h-16 h, then transferring it to 2×YT medium (16 g/L peptone, 10 g/L yeast extract, 5 g/L sodium chloride) at the ratio of 1:100 for amplification culturing, culturing at 37° C., 220 rpm until the $OD_{600}$ of the bacterial solution is 0.4-0.6, adding IPTG (Sigma Company, Cat. No.: I5502-1G) at a final concentration of 0.5 mM for inducing expression. The inducing conditions are 18° C., 180 rpm for 20 h. Finally, collecting the bacteria by centrifugation, and storing at −20° C. or immediately proceeding to the next step of purification.

4. Resuspending (1 L) the bacterial precipitation by using about 50 ml of phosphate buffer (pH 7.8) (40 mM sodium dihydrogen phosphate, 500 mM sodium chloride), and disrupting the bacteria by utilizing a high-pressure bacterium disrupting instrument (SCIENTZ BIO) prior to centrifuging at 13000 rpm for 30 min to fully isolate the soluble protein from the inclusion bodies.

5. Equilibrating the Ni-NTA (Qiagen company, Cat. No.: 30210) affinity column with 5 column volumes of binding buffer (40 mM $NaH_2PO_3$, 500 mM NaCl, pH 7.8). Then adding the protein supernatant and incubating at 4° C. for 0.5-1 h to allow the target recombinant protein fully bind to the column material. Then rinsing the impure proteins with 200 ml of washing buffer containing 10 mM imidazole (10 mM imidazole, 40 mM $NaH_2PO_3$, 500 mM NaCl, pH 7.8) (Sigma Company). If Trx-tagged target protein is needed, an elution buffer (250 mM imidazole, 40 mM $NaH_2PO_3$, 500 mM NaCl, pH 7.8) can be used directly to elute the target protein Trx-C17B3. If the Trx-tagged target protein needs to be removed, an appropriate amount of TEV protease with His tag can be added. After incubating at 4° C. for 16 h, collecting the flow-through fluid, which is the target collagen C17B3 with the carrier protein Trx removed.

6. The anion exchange column can be used for rapid purification of the target protein. Dialyzing the target protein into buffer A (20 mM Tris, 15 mM NaCl, pH 8.0), letting it flow through the anion exchange column Hitrap Q (GE Healthcare), and gradient eluting with buffer B (20 mM Tris, 1 M NaCl, pH 8.0), collecting different elution fractions to detect protein. Dialyzing the obtained target protein product overnight, and lyophilizing it into dry powder for later use.

7. Detecting the molecular weight and purity of the obtained C17B3 protein by SDS-PAGE. The specific process is: taking 40 μl of purified protein solution, adding 10 μl of 5× protein loading buffer (250 mM Tris-HCl (pH: 6.8), 10% SDS, 0.5% bromophenol blue, 50% glycerol, 5% β-mercaptoethanol), boiling in 100° C. boiling water at for 10 min, then adding 10 μl per well to SDS-PAGE protein gel, running at 80V for 2 h, and staining the protein with Coomassie Brilliant Blue Staining Solution (0.1% Coomassie Brilliant Blue R-250, 25% Isopropanol, 10% acetic acid glacial) for 20 min, then utilizing protein decolorizing solution (10% acetic acid, 5% ethanol) for decolorization. Finally, measuring the protein activity in comparison with human natural collagen.

Construction and Expression of C17C1 Gene Expression Vector

1. The full-length gene sequence of human-derived collagen C17C1 used in Example 2 is shown in SEQ ID No. 8. This sequence has been codon optimized for the codons of E. coli.

2. The full length of C17C1 gene is 357 bp. According to the optimized C17C1 codon gene sequence SEQ ID No. 8, Beijing Shengyuan Kemeng Gene Biotechnology Co., Ltd. is entrusted to synthesize the gene fragment, and after linking the synthesized C17C1 gene fragment to Tev protease restriction sites, the gene fragment is inserted to the PET32a expression vector (provided by the Institute of Biophysics, Chinese Academy of Sciences) through the Kpn I and Xho I restriction sites. The successfully constructed expression plasmid is transformed into E. coli competent cells BL21 (DE3) (Merck Company). The specific process is as follows: 1: taking 1 μl of this plasmid to 100 μl of E. coli competent cells BL21 (DE3), and letting it stand on ice for 30 min. 2: heat shocking the mixture in a 42° C. water bath for 90 s, then quickly placing it on ice and letting it stand for 2 min. 3: adding 600 μl of non-resistant LB to the mixture and culturing for 1 hour at 37° C., 220 rpm. 4: taking 200 μl of the bacterial solution and evenly spreading it on the ampicillin resistance-containing LB plate (10 g/L peptone, 5 g/L yeast extract, 10 g/L sodium chloride, 15 g/L agar, 100 μg/ml ampicillin antibiotics). 5: culturing the plate upside down in a 37° C. incubator for about 20 h until growing out clear and visible colonies.

3. Picking a single colony from the transformed LB plate and culturing it in 10 ml LB (containing 100 μg/ml ampicillin antibiotics) medium for 12 h-16 h, then transferring it to 2×YT medium (16 g/L peptone, 10 g/L yeast extract, 5 g/L sodium chloride) at the ratio of 1:100 for amplification culturing, culturing at 37° C., 220 rpm until the $OD_{600}$ of the bacterial solution is 0.4-0.6, adding IPTG (Sigma Company, Cat. No.: I5502-1G) at a final concentration of 0.5 mM for inducing expression. The inducing conditions are 18° C., 180 rpm for 20 h. Finally, collecting the bacteria by centrifugation, and storing at −20° C. or immediately proceeding to the next step of purification.

4. Resuspending (1 L) the bacterial precipitation by using about 50 ml of phosphate buffer (pH 7.8) (40 mM sodium dihydrogen phosphate, 500 mM sodium chloride), and disrupting the bacteria by utilizing a high-pressure bacterium disrupting instrument (SCIENTZ BIO) prior to centrifuging at 13000 rpm for 30 min to fully isolate the soluble protein from the inclusion bodies.

5. Equilibrating the Ni-NTA (Qiagen company, Cat. No.: 30210) affinity column with 5 column volumes of binding buffer (40 mM $NaH_2PO_3$, 500 mM NaCl, pH 7.8). Then adding the protein supernatant and incubating at 4° C. for 0.5-1 h to allow the target recombinant protein fully bind to the column material. Then rinsing the impure proteins with 200 ml of washing buffer containing 10 mM imidazole (10 mM imidazole, 40 mM $NaH_2PO_3$, 500 mM NaCl, pH 7.8) (Sigma Company). If Trx-tagged target protein is needed, an elution buffer (250 mM imidazole, 40 mM $NaH_2PO_3$, 500 mM NaCl, pH 7.8) can be used directly to elute the target protein Trx-C17C1. If the Trx-tagged target protein needs to be removed, an appropriate amount of TEV protease with His tag can be added. After incubating at 4° C. for 16 h, collecting the flow-through fluid, which is the target collagen C17C1 with the carrier protein Trx removed.

6. The anion exchange column can be used for rapid purification of the target protein. Dialyzing the target protein into buffer A (20 mM Tris, 15 mM NaCl, pH 8.0), letting it flow through the anion exchange column Hitrap Q (GE Healthcare), and gradient eluting with buffer B (20 mM Tris, 1 M NaCl, pH 8.0), collecting different elution fractions to detect protein. Dialyzing the obtained target protein product overnight, and lyophilizing it into dry powder for later use.

7. Detecting the molecular weight and purity of the obtained C17C1 protein by SDS-PAGE. The specific process is: taking 40 µl of purified protein solution, adding 10 µl of 5× protein loading buffer (250 mM Tris-HCl (pH: 6.8), 10% SDS, 0.5% bromophenol blue, 50% glycerol, 5% β-mercaptoethanol), boiling in 100° C. boiling water at for 10 min, then adding 10 µl per well to SDS-PAGE protein gel, running at 80V for 2 h, and staining the protein with Coomassie Brilliant Blue Staining Solution (0.1% Coomassie Brilliant Blue R-250, 25% Isopropanol, 10% acetic acid glacial) for 20 min, then utilizing protein decolorizing solution (10% acetic acid, 5% ethanol) for decolorization. Finally, measuring the protein activity in comparison with human natural collagen.

Results

Figure 2:
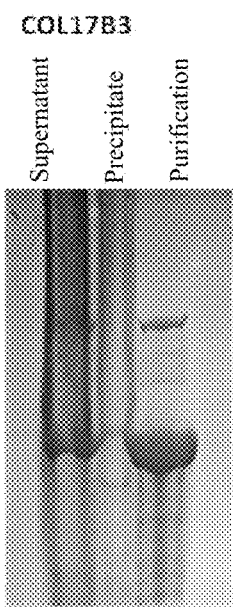
FIG. 2 is a protein electrophoresis diagram obtained after expression and purification of the Trx-C17B3 protein of the present invention; the molecular weight of the Trx-C17B3 protein detected by electrophoresis is about 40 kDa.
Figure 3:
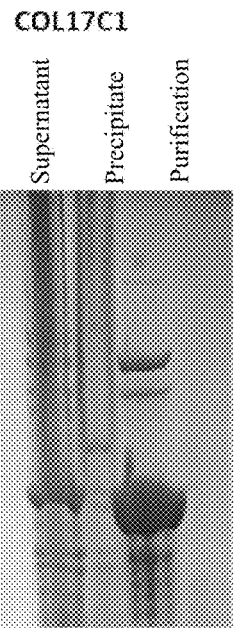
FIG. 3 is a protein electrophoresis diagram obtained after expression and purification of the Trx-C17C1 protein of the present invention; the molecular weight of the Trx-C17C1 protein detected by electrophoresis is about 32 kDa.

Electrophoresis diagrams of FIGS. 1-3 respectively show that Trx-C17A3, Trx-C17B3 and Trx-C17C1 fusion proteins with apparent molecular weights of 42 kDa, 40 kDa and 32 kDa are obtained.

Figure 4:
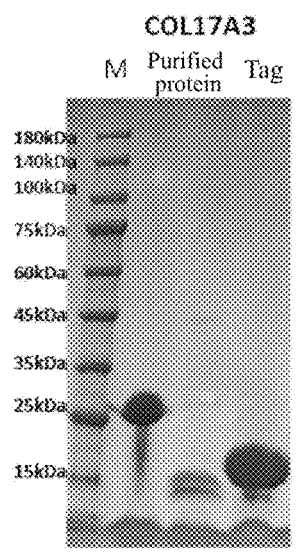
FIG. 4 is an electrophoresis diagram of the target protein C17A3 protein obtained after the expression of Trx-C17A3 protein, through restriction digestion to remove the Trx tag and ion exchange purification; the molecular weight of the C17A3 protein detected by electrophoresis is about 25 kDa, which corresponds to the protein with amino acid sequence of SEQ ID No. 4.
Figure 5:
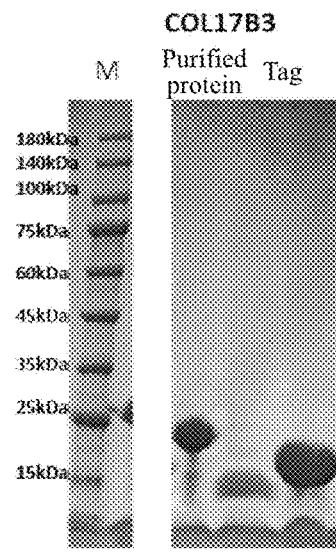
FIG. 5 is an electrophoresis diagram of the target protein C17B3 protein obtained after the expression of Trx-C17B3 protein, through restriction digestion to remove the Trx tag and ion exchange purification; the molecular weight of the C17B3 protein detected by electrophoresis is about 23 kDa, which corresponds to the protein with amino acid sequence of SEQ ID No. 6.
Figure 6:
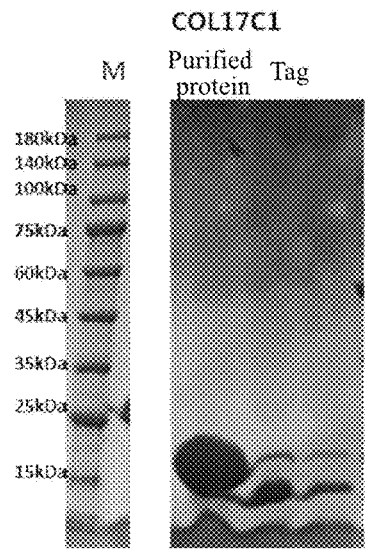
FIG. 6 is an electrophoresis diagram of the target protein C17C1 protein obtained after the expression of Trx-C17C1 protein, through restriction digestion to remove Trx tag and ion exchange purification; the molecular weight of C17C1 protein detected by electrophoresis is about 16 kDa, which corresponds to the protein with amino acid sequence of SEQ ID No. 3.

Electrophoresis diagrams of FIGS. 4-6 respectively show that C17A3, C17B3 and C17C1 fusion proteins with apparent molecular weights of 25 kDa, 23 kDa, and 16 kDa are obtained.

Example 2: Detection of Cell Adhesion Activity of C17A3, C17B3, and C17C1 Proteins For the detection method of collagen activity, please refer to the literature Juming Yao, Satoshi Yanagisawa, Tetsuo Asakura, Design, Expression and Characterization of Collagen-Like Proteins Based on the Cell Adhesive and Crosslinking Sequences Derived from Native Collagens, J Biochem. 136, 643-649 (2004). The specific implementation method is as follows:

1. Detecting the concentration of the protein sample to be detected including human collagen control (Sigma, C7774), C17A3, C17A1 (SEQ ID No. 1, prepared by the same method as C17A3), C17B3, C17B1 (SEQ ID No. 2, prepare by the same method as C17B3), and C17C1 protein samples by utilizing the ultraviolet (UV) absorption method. Specifically, determining the UV absorption of the samples at 215 nm and 225 nm, and calculating the protein concentrations by the empirical formula C(µg/mL)=144X(A215-A225). It should be noted that it needs to be detected when A215<1.5. The principle of this method is to determine the characteristic absorption of peptide bonds under far UV light, which is not affected by the content of chromophore, has less interference substances, and is simple to operate. It is suitable for detecting human collagen and its analogs that are not colored by Coomassie Brilliant Blue. (The reference is Walker J M. The Protein Protocols Handbook, second edition. Humana Press. 43-45). After detecting the protein concentrations, adjusting the concentrations of all detected proteins to 0.5 mg/ml with PBS.

2. Adding 100 µl of various protein solutions and PBS solution blank control to the 96-well plate, and letting it stand at room temperature for 60 min.

3. Adding $10^5$ well-cultured 3T3 cells (from Teacher Tong Pei, Tsinghua University) into each well, and incubating at 37° C. for 60 minutes.

4. Washing each well with PBS 4 times.

5. Detecting the absorbance at $OD_{492\ nm}$ with LDH detection kit (Roche, 04744926001). The absorbance at $OD_{492\ nm}$ can reflect the cell adhesion activity of collagen or its fragments. The higher the cell adhesion activity of the protein, the more it can provide cells with a high-quality external environment in a short time, helping cells adhere to the wall.

Figure 7:
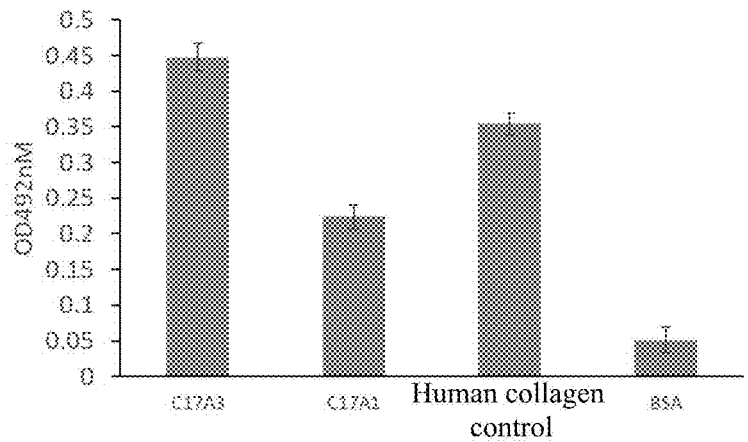
FIG. 7 shows the biological activity detection results of the C17A3 protein of the present invention compared with the C17A1 protein (SEQ ID No. 1) and human collagen.
Figure 8:
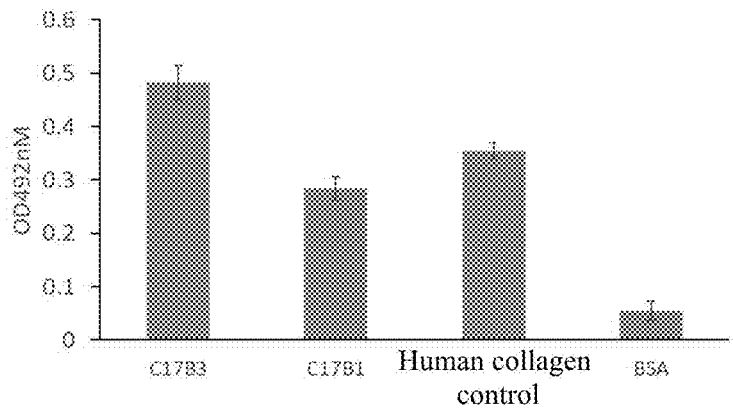
FIG. 8 shows the biological activity detection results of the C17B3 protein of the present invention compared with the C17B1 protein (SEQ ID No. 2) and human collagen.
Figure 9:
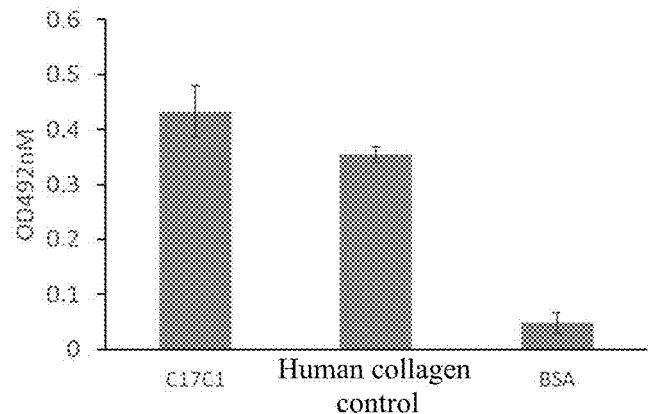
FIG. 9 shows the biological activity detection results of the C17C1 protein of the present invention compared with human collagen.

See FIGS. 7 to 9 for results. FIGS. 7 to 9 are plotted based on the average and standard error of $OD_{492\ nm}$ from three parallel experiments.

The results of FIGS. 7 to 9 show that the three human recombinant collagens (i.e., C17A3, C17B3, and C17C1) all have good cell adhesion activity compared with commercial human collagen.

Sequences
(C17A)
SEQ ID NO. 1
GSPGPKGDMGSPGPKGDRGFPGTPGIPGPLGHPGPQGPKGQKGSVGDPGM

EGPMGQRGREGPMGPRGEA (C17B)
SEQ ID NO. 2
GLQGLRGEVGLPGVKGDKGPMGPPGPKGDQGEKGPRGLTGEPGMRGLPGA

VGEPGAKGAMGPA (C17C1)
SEQ ID NO. 3
GADFAGDLDYNELAVRVSESMQRQGLLQGMAYTVQGPPGQPGPQGPPGIS

KVFSAYSNVTADLMDFFQTYGAIQGPPGQKGEMGTPGPKGDRGPAGPPGH

PGPPGPRGHKGEKGDKGDQ (C17A3)
SEQ ID NO. 4
GSPGPKGDMGSPGPKGDRGFPGTPGIPGPLGHPGPQGPKGQKGSVGDPGM

EGPMGQRGREGPMGPRGEAGSPGPKGDMGSPGPKGDRGFPGTPGIPGPLG

HPGPQGPKGQKGSVGDPGMEGPMGQRGREGPMGPRGEAGSPGPKGDMGSP

GPKGDRGFPGTPGIPGPLGHPGPQGPKGQKGSVGDPGMEGPMGQRGREGP

MGPRGEA (C17A3-DNA)
SEQ ID NO. 5
GGTAGCCCAGGTCCAAAAGGTGATATGGGAAGCCCAGGTCCGAAAGGTGA

TCGTGGTTTTCCGGGTACACCAGGTATTCCGGGTCCACTGGGTCATCCAG

GTCCGCAAGGTCCGAAAGGCCAGAAAGGTAGCGTGGGTGATCCGGGTATG

GAAGGGCCTATGGGGCAGCGTGGGCGTGAAGGGCCGATGGGTCCGCGTGG

TGAAGCAGGTAGCCCGGGGCCTAAAGGGGATATGGGGAGTCCGGGTCCGA

AAGGGGATCGTGGATTTCCGGGTACGCCGGGTATCCCGGGTCCGCTGGGT

CATCCGGGTCCGCAAGGGCCTAAAGGTCAGAAAGGTAGTGTGGGTGATCC

TGGTATGGAAGGTCCGATGGGTCAGCGTGGTCGTGAGGGTCCGATGGGAC

CGCGTGGTGAGGCTGGTAGCCCTGGTCCGAAAGGAGATATGGGTAGCCCG

GGTCCGAAAGGTGACCGTGGTTTTCCTGGTACACCGGGTATTCCAGGGCC

TCTGGGTCATCCTGGTCCTCAGGGTCCGAAAGGTCAGAAAGGGAGTGTGG

GAGATCCGGGTATGGAGGGTCCGATGGGGCAGCGCGGTCGTGAAGGTCCG

ATGGGCCCGCGTGGTGAAGCC (C17B3)
SEQ ID NO. 6
GLQGLRGEVGLPGVKGDKGPMGPPGPKGDQGEKGPRGLTGEPGMRGLPGA

VGEPGAKGAMGPAGLQGLRGEVGLPGVKGDKGPMGPPGPKGDQGEKGPRG

-continued

LTGEPGMRGLPGAVGEPGAKGAMGPAGLQGLRGEVGLPGVKGDKGPMGPP
GPKGDQGEKGPRGLTGEPGMRGLPGAVGEPGAKGAMGPA (C17B3-DNA)

SEQ ID NO. 7
GGTCTGCAGGGTCTGCGTGGTGAAGTAGGACTGCCGGGTGTGAAAGGAGA
TAAAGGACCAATGGGTCCACCAGGACCAAAAGGAGATCAAGGAGAAAAAG
GACCACGTGGTCTGACAGGTGAACCGGGTATGCGTGGGCTGCCGGGAGCA
GTTGGAGAACCGGGAGCAAAAGGAGCAATGGGTCCAGCAGGACTGCAGGG
TCTGCGCGGTGAAGTGGGACTGCCTGGTGTTAAAGGGGATAAAGGGCCGA
TGGGTCCGCCGGGTCCGAAAGGAGATCAGGGAGAAAAAGGGCCGCGTGGT
CTGACCGGTGAACCGGGAATGCGTGGTCTGCCGGGGGCTGTGGGTGAGCC
AGGTGCAAAAGGTGCAATGGGTCCTGCAGGTCTGCAAGGACTGCGTGGAG
AAGTGGGTCTGCCTGGTGTGAAAGGTGATAAAGGTCCGATGGGTCCTCCG
GGTCCGAAAGGTGATCAGGGTGAAAAAGGTCCGCGTGGTCTGACGGGTGA
ACCGGGCATGCGTGGTCTGCCTGGGGCAGTTGGTGAACCGGGGGCAAAAG
GTGCTATGGGGCCGGCA (C17C1-DNA)

SEQ ID NO. 8
GGTGCAGATTTTGCAGGTGATCTGGATTATAATGAACTGGCAGTTCGTGT
TAGCGAAAGCATGCAGCGTCAGGGACTGCTGCAGGGAATGGCATATACCG
TTCAGGGTCCGCCGGGTCAGCCGGGTCCTCAAGGTCCTCCTGGTATTAGC
AAAGTTTTTAGTGCATATTCAAACGTGACGGCAGATCTGATGGATTTTTT
TCAGACGTATGGTGCAATTCAGGGTCCTCCTGGGCAAAAAGGTGAAATGG
GTACACCTGGTCCGAAAGGCGATCGTGGTCCGGCCGGTCCGCCGGGCCAC
CCTGGTCCTCCTGGCCCTCGTGGTCATAAAGGTGAGAAAGGTGATAAGG
TGATCAA (COL17A1)

SEQ ID NO. 9
MDVTKKNKRDGTEVTERIVTETVTTRLTSLPPKGGTSNGYAKTASLGGGS
RLEKQSLTHGSSGYINSTGSTRGHASTSSYRRAHSPASTLPNSPGSTFER
KTHVTRHAYEGSSSGNSSPEYPRKEFASSSTRGRSQTRESEIRVRLQSAS
PSTRWTELDDVKRLLKGSRSASVSPTRNSSNTLPIPKKGTVETKIVTASS
QSVSGTYDATILDANLPSHVWSSTLPAGSSMGTYIThNMTTQSSSLLNTN
AYSAGSVFGVPNNMASCSPTLHPGLSTSSSVFGMQNNLAPSLTTLSHGTT
TTSTAYGVKKNMPQSPAAVNTGVSTSAACTTSVQSDDLLHKDCKFLILEK
DNTPAKKEMELLIMTKDSGKVFTASPASIAATSFSEDTLKKEKQAAYNAD
SGLKAEANGDLKTVSTKGKTTTADIHSYGSSGGGGSGGGGGVGGAGGGPW
GPAPAWCPCGSCCSWWKWLLGLLLTWLLLLGLLFGLIALAEEVRKLKARV
DELERIRRSILPYGDSMDRIEKDRLQGMAPAAGADLDKIGLHSDSQEELW
MFVRKKLMMEQENGNLRGSPGPKGDMGSPGPKGDRGFPGTPGIPGPLGHP
GPQGPKGQKGSVGDPGMEGPMGQRGREGPMGPRGEAGPPGSGEKGERGAA
GEPGPHGPPGVPGSVGPKGSSGSPGPQGPPGPVGLQGLRGEVGLPGVKGD
KGPMGPPGPKGDQGEKGPRGLTGEPGMRGLPGAVGEPGAKGAMGPAGPDG
HQGPRGEQGLTGMPGIRGPPGPSGDPGKPGLTGPQGPQGLPGTPGRPGIK
GEPGAPGKIVTSEGSSMLTVPGPPGPPGAMGPPGPPGAPGPAGPAGLPGH
QEVLNLQGPPGPPGPRGPPGPSIPGPPGPRGPPGEGLPGPPGPPGSFLSN
SETFLSGPPGPPGPPGPKGDQGPPGPRGHQGEQGLPGFSTSGSSSFGLNL
QGPPGPPGPQGPKGDKGDPGVPGALGIPSGPSEGGSSSTMYVSGPPGPPG
PPGPPGSISSSGQEIQQYISEYMQSDSIRSYLSGVQGPPGPPGPPGPVTT
ITGETFDYSELASHVVSYLRTSGYGVSLFSSSISSEDILAVLQRDDVRQY
LRQYLMGPRGPPGPPGASGDGSLLSLDYAELSSRILSYMSSSGISIGLPG
PPGPPGLPGTSYEELLSLLRGSEFRGIVGPPGPPGPPGIPGNVWSSISVE
DLSSYLHTAGLSFIPGPPGPPGPPGPRGPPGVSGALATYAAENSDSFRSE
LISYLTSPDVRSFIVGPPGPPGPQGPPGDSRLLSTDASHSRGSSSSHSS
SVRRGSSYSSSMSTGGGGAGSLGAGGAFGEAAGDRGPYGTDIGPGGGYGA
AAEGGMYAGNGGLLGADFAGDLDYNELAVRVSESMQRQGLLQGMAYTVQG
PPGQPGPQGPPGISKVFSAYSNVTADLMDFFQTYGAIQGPPGQKGEMGTP
GPKGDRGPAGPPGHPGPPGPRGHKGEKGDKGDQVYAGRRRRRSIAVKP

The invention claimed is:

1. A polypeptide comprising a sequence represented by $(A)_m$, wherein each A consists of the amino acid sequence of SEQ ID NO: 1; the amino acid sequence of SEQ ID NO: 1 with 1, 2, 3, 4, or 5 amino acid residue(s) substituted, added, or deleted; or an amino acid sequence having 90%, 91%, 92%, 93%, 94%, 95%, 96%, or 97% identity to SEQ ID NO: 1; wherein m is 3, each A is the same, and two adjacent As are directly linked by a peptide bond; and wherein the polypeptide has cell adhesion activity.

2. The polypeptide of claim 1, comprising the amino acid sequence of SEQ ID NO: 4.

3. A composition comprising the polypeptide of claim 1.

4. An article comprising the polypeptide of claim 1, which is a pharmaceutical composition, a medical device, a tissue engineering product, cosmetics, or a health product.

5. The article of claim 4, wherein the article is a pharmaceutical composition, and the pharmaceutical composition is a topical preparation.

6. The article of claim 5, wherein the topical preparation is a topical gel further comprising a pharmaceutically acceptable carrier.

7. A method for the preparation of an article, comprising making an article by utilizing the polypeptide of claim 1.

8. The method of claim 7, wherein the article is a medical device, a tissue engineering product, a cosmetic product, or a health product.

* * * * *